| United States Patent [19] | [11] | 4,116,994 |
|---|---|---|
| Vannice et al. | [45] | Sep. 26, 1978 |

[54] HYDROCARBON SYNTHESIS FROM CO AND $H_2$ USING RH SUPPORTED ON TITANIUM OXIDES

[75] Inventors: M. Albert Vannice, Plainfield; Robert L. Garten, Summit, both of N.J.

[73] Assignee: Exxon Research & Engineering Co., Linden, N.J.

[21] Appl. No.: 819,871

[22] Filed: Jul. 28, 1977

Related U.S. Application Data

[63] Continuation of Ser. No. 673,358, Apr. 5, 1976, abandoned.

[51] Int. Cl.$^2$ .................................................. C07C 1/04
[52] U.S. Cl. ................................. 260/449 R; 252/460; 252/466 PT
[58] Field of Search ..................... 260/449 R, 449.6 R

[56] References Cited

U.S. PATENT DOCUMENTS

| 2,464,532 | 3/1949 | Sellers | 260/449.6 |
| 2,637,739 | 5/1953 | McGrath | 260/449.6 |
| 2,699,988 | 1/1955 | McGrath | 260/449.6 |
| 2,850,515 | 9/1958 | Riblett et al. | 260/449.6 |

OTHER PUBLICATIONS

Eidus et al., Izvestia Akad Nauk SSSR, Ser Khim No. 7 (pp. 1160-1169) Translation pp. 1129-1135, Jul. 1965.
Kratel, Doctoral Dissertation, Technical University of Berlin, Charlottenburg, 1937, pp. 62-72, Kaiser Wilhelm Inst at Mulheim-Ruhr.
Pichler, Brenn. Chem., 19, pp. 226-230, 1938.
Shultz et al., Report of Investigations 6974, Bureau of Mines 1967, pp. 1-3, 5-14, 18.

*Primary Examiner*—Howard T. Mars
*Attorney, Agent, or Firm*—Joseph J. Allocca

[57] ABSTRACT

A new method for the selective synthesis of olefinic hydrocarbons of from $C_2$-$C_5$ from CO and $H_2$ which method comprises the steps of passing a synthesis gas stream of CO and $H_2$ at a $H_2$/CO ratio of from 0.1-10 at a space velocity of from 100 hr.$^{-1}$ to 50,000 hr.$^{-1}$ over a catalyst system comprising from 0.01 to 10 wt. % rhodium deposited on $TiO_2$, other titanium-containing oxides or mixtures of said titanium-containing oxides for a time sufficient to effect the generation of desired olefinic products, at a temperature of from 100°-500° C. and a pressure of from 100 to $10^5$ kPa. The supported rhodium catalyst has a surface area of from 10 to 60 $m^2g^{-1}$ of total catalyst with a preferred rhodium crystallite size $\leq$ 5 nm.

Rhodium supported on $TiO_2$, other titanium-containing oxides, or mixtures of titanium oxides results in a catalyst system which exhibits superior hydrocarbon synthesis characteristics. Such supported rhodium catalysts exhibit selectivity to olefinic products of from 2 to 5 carbons inclusive in processes for olefin generation accompanied by greater product yields and exhibit improved longevity, tolerance to sulfur and activity maintenance.

21 Claims, No Drawings

HYDROCARBON SYNTHESIS FROM CO AND $H_2$ USING RH SUPPORTED ON TITANIUM OXIDES

This is a continuation, of application Ser. No. 673,358, filed 4/5/76 and now abandoned.

Rhodium catalysts for the production of higher molecular weight hydrocarbons from CO and $H_2$ have been reported only in a Bureau of Mines Study (J. F. Shultz et al., U.S. Bureau of Mines Report #6974, 1967). This study showed that rhodium supported on $Al_2O_3$ produced 95+ wt. % methane at typical $H_2/CO$ ratios, 2163 kPa pressure and at temperatures from 440°–580° C. Because of its expense and low activity compared to other metals, rhodium was reported by these workers to be unattractive as a methanation catalyst.

It has been found, however, that rhodium dispersed on $TiO_2$ or other titanium-containing oxide supports has high activity and altered selectivity. Compared to $Al_2O_3$-supported rhodium, the use of $TiO_2$ or titanium-containing oxide-supported metal in olefin preparation processes results in a process which exhibits a marked decrease in methane in the products with a concomitant increase in the formation of higher molecular weight paraffins and olefins.

DESCRIPTION OF THE INVENTION

A new method for the improved synthesis of olefinic hydrocarbons and particularly olefins of from $C_2$ to $C_5$ chain length inclusive, and most particularly, $C_3$ and $C_4$ hydrocarbons from CO and $H_2$, which method comprises the steps of passing a synthesis gas stream comprising CO and $H_2$ at a $H_2/CO$ ratio of from 0.1–10, preferably 0.5–4, most preferably 1–3 at a space velocity of from 100 $hr^{-1}$ to 50,000 $hu^{-1}$ over a catalyst comprising from 0.01 to 10 wt. % rhodium on $TiO_2$, other titanium-containing oxides or mixtures thereof for a time sufficient to effect the generation of desired olefinic hydrocarbon products in the desired ratio, said contacting being effected at a temperature of from 100° to 500° C., preferably 150°–400° C., most preferably 150°–300° C. and a pressure of from 100 to $10^5$ kPa, preferably 100 to 3000 kPa, most preferably 100–2000 kPa. The supported rhodium catalyst system used in the instant process has a total BET surface area of from 10 to 60 $m^2g^{-1}$ with a rhodium crystallite size of preferably less than 5 nm.

Rhodium supported on $TiO_2$, other titanium-containing oxides or mixtures of titanium oxides results in a catalyst system which exhibits superior hydrocarbon synthesis characteristics in synthesis processes. The titanium-containing oxide supports which may be used in the practice of this invention are oxides having surface areas of from 1 to 200 $m^2g^{-1}$, preferably 10–100 $m^2g^{-1}$, most preferably, 25–100 $m^2g^{-1}$. The oxides are selected from the group comprising $TiO_2$, $Al_2O_3$-$TiO_2$, $SiO_2$-$TiO_2$, $TiO_2$-carbon, $ZrTiO_4$, alkaline earth titanates ($BaTiO_3$, $CaTiO_3$, $SrTiO_3$, $MgTiO_3$), alkali titanates ($Na_2TiO_3$, $K_2KiO_3$, $Li_2TiO_3$), and rare earth titanates. Preferably, the titanium oxide is $TiO_2$. With most supported metal catalysts, the higher the surface area of the support the higher the dispersion of the supported metal at a given metal loading. It is therefore desirable to use a $TiO_2$ with as high a surface area as possible to maximize the dispersion of the rhodium metal. However, when working with $TiO_2$, samples with surface areas of 150 to 250 $m^2g^{-1}$ (usually prepared by precipitation techniques) desurface on heating to ~500° C. Commercially available $TiO_2$ made by flame hydrolysis of $TiCl_4$ has a stable surface area of ~60 $m^2g^{-1}$ for thermal treatments at temperatures of ~500° C. or more and is therefore the preferred support. For thermal treatments at temperatures below 500° C., $TiO_2$ prepared by precipitation technique may be successfully employed.

Rhodium is deposited on the chosen support in a concentration of from 0.01 to 10 wt. %, preferably 0.05–5 wt. %, most preferably 0.1–2 wt. %, with the rhodium possessing a crystallite size, as determined by standard techniques such as X-ray diffraction or transmission electron microscopy of from 1 to 20 nm, preferably 1–10 nm, most preferably 1–5 nm.

Using standard experimental techniques, for a rhodium on $TiO_2$ system reduced in hydrogen at 450° C, X-ray diffraction shows no particles of rhodium in the reduced catalyst which indicates that the rhodium crystallites possess an average size of less than 5 nm, which corresponds to a dispersion of greater than 20%.

Rhodium catalysts supported on $TiO_2$, other titanium-containing oxides or mixtures thereof exhibit enhanced selectively to olefin products, especially $C_2$–$C_5$ inclusive olefins, most particularly $C_3$ and $C_4$ hydrocarbons. Such catalysts, when used in the present system exhibit enhanced activity, improved selectivity to said olefins, improved longevity and tolerance to sulfur as compared with rhodium catalysts of the prior art which are supported on materials such as $Al_2O_3$, $SiO_2$ or carbon.

The rhodium catalysts employed in the practice of the instant process are themselves prepared by techniques known in the art for the preparation of other catalyst systems, such as rhodium on $Al_2O_3$, etc. A suitable rhodium salt, such as rhodium chloride, rhodium nitrate or rhodium acetate, etc. is dissolved in a solvent such as water or any suitable solvent and stirred with the chosen titanium oxide system. Preferably, the support is $TiO_2$ prepared by flame hydrolysis of $TiCl_4$, which $TiO_2$ has a surface area of ~60 $m^2g^{-1}$. After thorough mixing the mixture is allowed to dry and then heat treated in air at a temperature of from 100° to 150° C or alternatively, it may be dried immediately by heating in air at a temperature of between 100° to 150° C for several hours.

The final step, however, which is essential to the successful practice of the instant invention is the step of heat treating the supported rhodium catalyst, prepared as outlined above, or by similar techniques, in a reducing atmosphere such as hydrogen at a temperature greater than 300° C. preferably greater than 400° C, most preferably greater than 500° C, for from 0.5 to 4 hours, preferably 1 to 2 hours.

Use of the above-identified catalyst in the instant process at reaction conditions equivalent to those of the prior art gives superior results (in the way of improved selectivity and greater product yields) when catalysts possessing rhodium with loadings equal to those of the prior art are used.

EXAMPLE 1

Rhodium catalysts with improved selectivity to hydrocarbons with carbon chain lengths of two to five carbon atoms and improved selectivity to olefinic hydrocarbons in this carbon number range are obtained by depositing rhodium on $TiO_2$ and other titanium-containing oxide supports. Thus, a 2 wt. % $Rh/TiO_2$ catalyst is prepared by stirring together 20 grams of $TiO_2$ with 4.08 ml of $RhCl_3$ solution containing 0.408 grams of rhodium. The $TiO_2$ was prepared by the flame hydrolysis of $TiCl_4$ and had a surface area of 60 $m^2g^{-1}$. Titania prepared by other techniques such as precipitation and calcination of a suitable salt is also satisfactory. After thoroughly mixing the $TiO_2$ and rhodium solution the mixture is dried in air at 120° C overnight.

To illustrate the desirable characteristics of $Rh/TiO_2$ it was compared to rhodium dispersed on $Al_2O_3$. Thus a 2% $Rh/Al_2O_3$ catalyst was prepared by mixing 5 grams of $Al_2O_3$ with 3.52 ml of $RhCl_3$ solution containing 0.102 grams of rhodium. The resulting mixture was dried in air at 110°–120° C overnight.

Table I illustrates the desirable characteristics of $TiO_2$ or titanium-containing oxide-supported rhodium catalysts. The $Rh/TiO_2$ shows improved selectivity to hydrocarbons with carbon chain lengths of two to five hydrocarbons at all $H_2/CO$ ratios. Thus, at an $H_2/CO$ ratio of 1.6, 26 mole % of the products are $C_2$–$C_5$ hydrocarbons whereas $Rh/Al_2O_3$ produces only 14 mole % hydrocarbons in this carbon number range. $Rh/TiO_2$ also shows increased selectivity to olefins compared to $Rh/Al_2O_3$. As Table 1 demonstrates the ratio of ethylene to ethane is greater at all conditions for $Rh/TiO_2$ compared to $Rh/Al_2O_3$. $Rh/TiO_2$ thus exhibits the desirable characteristic of improved selectivity to $C_2$–$C_5$ hydrocarbons and olefins, these hydrocarbons being highly desirable as chemical intermediates for the production of plastics, rubbers, alcohols, ketones, aldehydes, esters and acids.

Table 1

Selectivities of Rhodium Catalysts
(Reaction Conditions: Pressure = 100 kPa)

| Catalyst[a] | Temp. (° C) | % CO Conv. | $H_2$/CO | Mole Product % | | | | | | |
|---|---|---|---|---|---|---|---|---|---|---|
| | | | | $CH_4$ | $C_2H_4$ | $C_2H_6$ | $C_3H_6$/$C_3H_8$ | $C_4H_8$/$C_4H_{10}$ | $C_5H_{10}$/$C_5H_{12}$ | $C_6^+$ |
| 2% $Rh/TiO_2$ | 248 | 0.3 | 0.6 | 63 | 7 | 0 | 19 | 12 | 0 | 0 |
| | | 1.3 | 1.6 | 74 | 3 | 2 | 14 | 5 | 1 | 0 |
| | | 3.3 | 3.0 | 80 | 2 | 3 | 11 | 3 | 2 | 0 |
| | | 5.3 | 6.0 | 86 | 1 | 4 | 7 | 2 | 1 | 0 |
| 2% $Rh/Al_2O_3$ | 265 | 1.6 | 0.6 | 74 | 2 | 14 | 6 | 3 | 1 | 0 |
| | | 3.5 | 1.6 | 85 | 0 | 10 | 3 | 1 | 0 | 0 |
| | | 5.2 | 3.0 | 90 | 0 | 8 | 2 | 1 | 0 | 0 |
| | | 13.9 | 6.0 | 93 | 0 | 5 | 2 | 1 | 0 | 0 |

[a] Each catalyst reduced 1 hour at 450° C before feed introduced at reaction temperature.

What is claimed is:

1. A process for the enhanced synthesis of olefins and paraffins, wherein said paraffins are other than methane, comprising the steps of passing $H_2$ and CO in a $H_2$/CO ratio of 0.1 to 10 over a catalyst comprising rhodium on a titanium-containing oxide support, wherein said titanium-containing oxide support is selected from the group consisting of $TiO_2$, $ZrTiO_4$, $TiO_2$-carbon, $TiO_2$-$Al_2O_3$, $TiO_2$-$SiO_2$, alkaline earth titanates, alkali titanates, rare earth titanates and mixtures thereof, at a space velocity of from 100 to 50,000 V/V/Hr and at a temperature of from 100° to 500° C., at a pressure of from 100 to $10^5$ kPa for a time sufficient to effect the generation of the desired olefinic and paraffinic products in the desired ratio, wherein the concentration of said rhodium in said catalyst is from 0.01 to 10% by weight.

2. The process of claim 1 wherein the titanium-containing oxide is $TiO_2$.

3. The process of claim 2 wherein the rhodium on titanium oxide catalyst has a weight loading of rhodium of from 0.1 to 2 wt. % based on total catalyst.

4. The process of claim 2 wherein the rhodium on titanium oxide catalyst has a rhodium crystallite size of from 1 to 5 nm.

5. The process of claim 2 wherein the $H_2$/CO ratio is from 4.0 to 0.5, the temperature is from 150° to 400° C. and the pressure is from 100 to 3000 kPa.

6. The process of claim 2 wherein the $H_2$/CO ratio is from 3 to 1, the temperature is from 150° to 300° C and the pressure is from 100 to 2000 kPa.

7. The process of claim 2 wherein the rhodium concentration is from 0.05 to 5 wt. %.

8. The process of claim 2 wherein the catalyst comprising rhodium supported on $TiO_2$ has a rhodium particle crystallite size of from 1 to 20 nm.

9. The process of claim 2 wherein the catalyst comprising rhodium supported on $TiO_2$ has a rhodium particle crystallite size of from 1 to 10 nm.

10. The process of claim 2 wherein the $TiO_2$ has a surface area of from 1–200 $m^2g^{-1}$.

11. The process of claim 2 wherein the $TiO_2$ has a surface area of from 25–100 $m^2g^{-1}$.

12. The process of claim 1 wherein the titanium-containing oxide has a surface area of from 1 to 200 $m^2g^{-1}$.

13. The process of claim 1 wherein the rhodium concentration is from 0.1 to 2 wt. %.

14. The process of claim 1 wherein the catalyst comprising rhodium supported on a titanium-containing oxide has a rhodium particle crystallite size of from 1 to 20 nm.

15. The process of claim 13 wherein the catalyst comprising rhodium supported on a titanium-containing oxide has a rhodium particle crystallite size of from 1 to 5 nm.

16. The process of claim 1 wherein the rhodium concentration is from 0.05 to 5 wt. %.

17. The process of claim 1 wherein the catalyst comprising rhodium supported on a titanium-containing oxide has a rhodium particle crystallite size of from 1 to 10 nm.

18. The process of claim 1 wherein the $H_2$/CO ratio is from 4.0 to 0.5, the temperature is from 150° to 400° C. and the pressure is from 100 to 3000 kPa.

19. The process of claim 1 wherein the $H_2$/CO ratio is from 3 to 1, the temperature is from 150° to 300° C. and the pressure is from 100 to 2000 kPa.

20. The process of claim 1 wherein the titanium-containing oxide has a surface area of from 10–100 $m^2g^{-1}$.

21. The process of claim 1 wherein the titanium-containing oxide has a surface area of from 25–100 $m^2g^{-1}$.